(12) United States Patent
Abate et al.

(10) Patent No.: US 10,882,055 B2
(45) Date of Patent: Jan. 5, 2021

(54) IONIZATION AIR PURIFICATION SYSTEM FOR THE PASSENGER CABIN OF A VEHICLE

(71) Applicant: CLEAN AIR GROUP, INC., Fairfield, CT (US)

(72) Inventors: Anthony M. Abate, Seymour, CT (US); Hal Ross Gurman, Scottsdale, AZ (US)

(73) Assignee: CLEAN AIR GROUP, INC., Fairfield, CT (US)

( * ) Notice: Subject to any disclaimer, the term of this patent is extended or adjusted under 35 U.S.C. 154(b) by 350 days.

(21) Appl. No.: 15/790,525

(22) Filed: Oct. 23, 2017

(65) Prior Publication Data

US 2018/0065126 A1    Mar. 8, 2018

Related U.S. Application Data

(63) Continuation-in-part of application No. 14/385,346, filed as application No. PCT/US2013/032163 on Mar. 15, 2013.
(Continued)

(51) Int. Cl.
*B03C 3/68* (2006.01)
*B60H 3/00* (2006.01)
(Continued)

(52) U.S. Cl.
CPC .................. *B03C 3/68* (2013.01); *A61L 9/22* (2013.01); *B01D 46/0078* (2013.01); *B03C 3/41* (2013.01); *B60H 1/00371* (2013.01); *B60H 3/0078* (2013.01); *B60H 3/0633* (2013.01); *B61D 27/00* (2013.01); *B64D 13/00* (2013.01);
(Continued)

(58) Field of Classification Search
USPC ................................ 96/16, 19; 361/230, 231
See application file for complete search history.

(56) References Cited

U.S. PATENT DOCUMENTS 3,417,302 A * 12/1968 Holger ..................... A61N 1/44
                                                                361/231
3,798,922 A *  3/1974 Duke ........................ F24F 3/166
                                                                  62/264
(Continued)

FOREIGN PATENT DOCUMENTS

DE            19651403 A1 *  6/1998  .............. F24F 3/166

*Primary Examiner* — Christopher P Jones
*Assistant Examiner* — Sonji Turner
(74) *Attorney, Agent, or Firm* — Abelman, Frayne & Schwab

(57) ABSTRACT

An ionization air purification system for the passenger cabin of vehicles, which modifies the degree of ionization by modifying the energy levels applied to an air ionization device having a tubular dielectric member or a planar dielectric member or ionization source proportional to the change in air flow dynamics and air quality. In one embodiment, an ionization air purification system for the passenger cabin of a vehicle is disclosed. The system includes an ionization device for purifying the air prior to entering into the passenger cabin of the vehicle while minimizing the production of ozone as a by-product; and means for modifying the degree of ionization by modifying the energy levels applied to the ionization tube or ionization source proportional to the change in air flow dynamics or air quality.

18 Claims, 16 Drawing Sheets

Related U.S. Application Data

(60) Provisional application No. 61/611,676, filed on Mar. 16, 2012.

(51) Int. Cl.
  *B03C 3/41* (2006.01)
  *B01D 46/00* (2006.01)
  *A61L 9/22* (2006.01)
  *B60H 3/06* (2006.01)
  *B64D 13/00* (2006.01)
  *B60H 1/00* (2006.01)
  *H01T 23/00* (2006.01)
  *B61D 27/00* (2006.01)
  *B64D 13/06* (2006.01)

(52) U.S. Cl.
  CPC ........... *H01T 23/00* (2013.01); *A61L 2209/11* (2013.01); *A61L 2209/111* (2013.01); *A61L 2209/14* (2013.01); *A61L 2209/16* (2013.01); *A61L 2209/21* (2013.01); *B01D 46/0028* (2013.01); *B03C 2201/04* (2013.01); *B03C 2201/30* (2013.01); *B64D 2013/067* (2013.01)

(56) References Cited

U.S. PATENT DOCUMENTS

| | | | | |
|---|---|---|---|---|
| 4,574,004 A * | 3/1986 | Schmidt-Ott | ...... | G01N 15/0266 250/283 |
| 4,911,737 A * | 3/1990 | Yehl | ...... | A61N 1/10 361/231 |
| 5,456,741 A * | 10/1995 | Takahara | ...... | B03C 3/12 95/6 |
| 5,501,844 A * | 3/1996 | Kasting, Jr. | ...... | A61L 9/015 422/186.15 |
| 5,942,026 A * | 8/1999 | Erlichman | ...... | F02M 25/12 123/198 E |
| 6,375,714 B1 * | 4/2002 | Rump | ...... | F24F 3/166 95/3 |
| 6,602,330 B2 * | 8/2003 | Allen | ...... | B60H 3/0071 55/385.3 |
| 6,668,563 B2 * | 12/2003 | Mirowsky | ...... | B64D 13/00 315/111.91 |
| 6,769,420 B1 * | 8/2004 | Motouchi | ...... | A61L 2/202 123/539 |
| 9,114,356 B2 * | 8/2015 | Gurman | ...... | B60H 3/0071 55/385.3 |
| 2003/0003028 A1 * | 1/2003 | Tomaselli | ...... | A61L 9/20 422/121 |
| 2005/0031503 A1 * | 2/2005 | Fox | ...... | A61L 9/22 422/186.04 |
| 2005/0058582 A1 * | 3/2005 | Paumier | ...... | B64D 13/00 315/111.91 |
| 2005/0142045 A1 * | 6/2005 | Yuen | ...... | F24F 3/166 95/3 |
| 2005/0186108 A1 * | 8/2005 | Fields | ...... | F02M 25/12 123/198 E |
| 2007/0051902 A1 * | 3/2007 | Justel | ...... | A61L 9/015 422/186.15 |
| 2007/0165353 A1 * | 7/2007 | Fleischer | ...... | B03C 3/12 95/6 |
| 2009/0017742 A1 * | 1/2009 | Diaks | ...... | A61N 1/10 361/231 |
| 2009/0042502 A1 * | 2/2009 | Kim | ...... | G01N 15/0266 250/283 |
| 2011/0096457 A1 * | 4/2011 | Gefter | ...... | F24F 3/166 62/264 |
| 2012/0212876 A1 * | 8/2012 | Rais | ...... | A61N 1/44 361/231 |

* cited by examiner

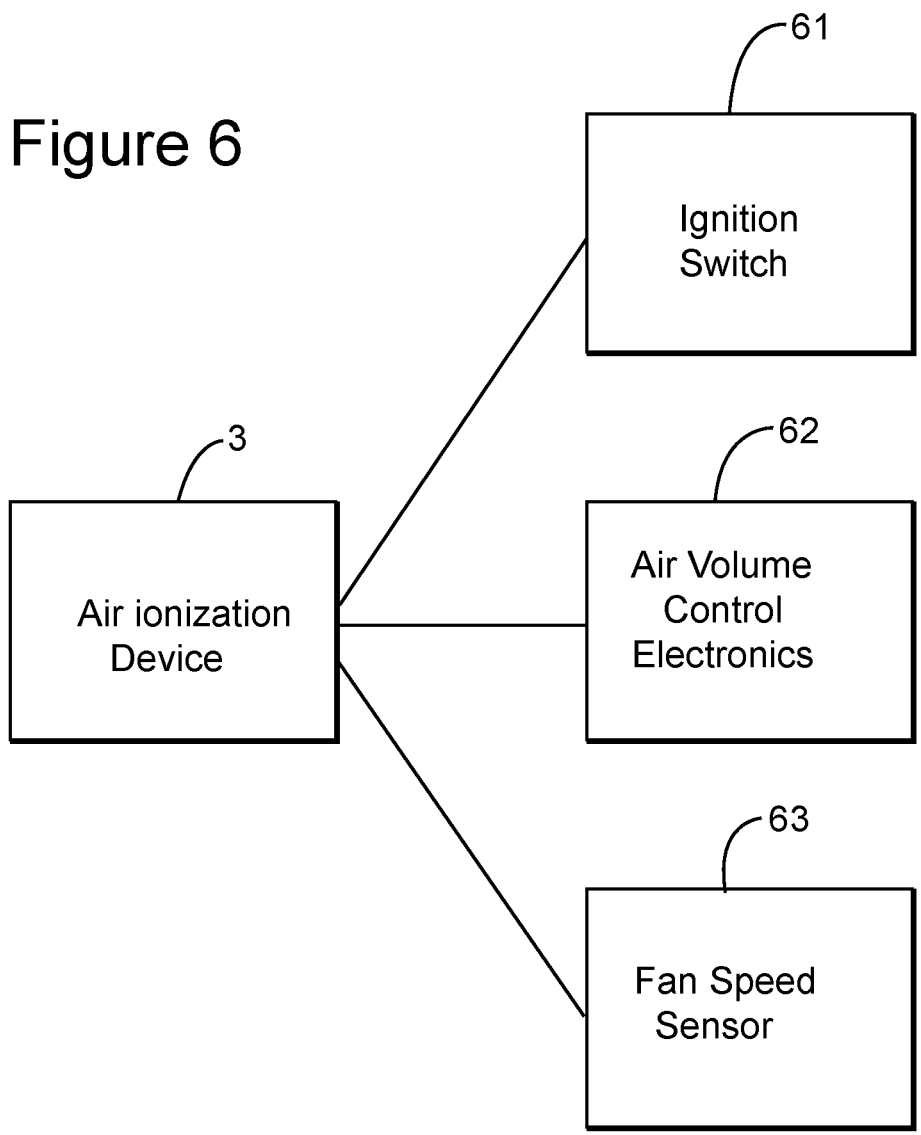

IONIZATION AIR PURIFICATION SYSTEM FOR THE PASSENGER CABIN OF A VEHICLE

CROSS REFERENCE TO RELATED APPLICATION

This application is a continuation-in-part of U.S. application Ser. No. 14/385,346, filed Sep. 15, 2014, which is a national phase of PCT Application No. PCT/US2013/032163, filed Mar. 15, 2013, which claims the benefit of U.S. Provisional Application No. 61/611,676, filed Mar. 16, 2012, all of which are hereby incorporated by reference.

FIELD OF THE INVENTION

The present invention relates to the use of air purification ionization systems in the field of transportation including, without limitation, cars, buses, trains, airplanes, trucks and other vehicles by which people and/or animals travel.

BACKGROUND OF THE INVENTION

Systems that employ ionization as a means for removing contaminants, both solid and gaseous from an air stream are known. One of the most popular uses of the technology is in products offered by ATMOSAIR™, both stand alone systems such as towers as well as systems that are installed within HVAC systems in homes and commercial buildings. As well, technology particularly suitable for the ionization process is more fully described in U.S. Patent Application Publication No. US 2010/0247389 A1 entitled "Bipoloar Ionization Tube" owned by the assignee of this invention and whose disclosure is also incorporated by reference herein. Other technology particularly suitable for the ionization process is more fully described in U.S. Patent Application Publication No. US 2014/0079596 A1 entitled "Fiberglass Dielectric Barrier Ionization Discharge Device" owned by the assignee of this invention and whose disclosure is also incorporated by reference herein.

It is believed that there are no commercially available systems that address problems unique to passenger vehicles which include variable air flow parameters which are subject to significant variation in air flow and the significant, but often varying changes in air quality, particularly with regard to gaseous pollutants which are often encountered, all of which can have significant impact on the efficiency and efficacy of the ionization system.

FIG. 1 depicts in general schematic form the air flow system within a typical passenger automobile, wherein the air flow passes through a cabin air filter 1 prior to entering the passenger cabin.

Referring to FIG. 2 in which a typical passenger bus air circulation system 10 is schematically depicted, as is often the case with passenger buses or larger land vehicles, the air handler is larger and is often mounted in the rear of or on the roof 11 of the bus as shown.

As illustrated in FIG. 3, a typical passenger train air conditioning system 30 is illustrated, which is not dissimilar from that described with regard to a passenger bus. Various sensors determine air flow and air quality and whether the system is in a fresh air or air circulation mode.

Referring next to FIG. 4, the air circulation system in most passenger planes generally has air flow controls which can be turned on or off—or modified as to the degree of flow—by individual passengers at their seats. Once the plane is airborne the system is generally a recirculation system. Indeed there is much discussion in literature that the constant recirculation of unpurified air within air craft has had adverse affects upon the health of passengers as they are constantly exposed to the same recirculated air.

Although the potential benefits of an ionization system in the field of transportation would have many benefits, to date no one has created a system particularly suitable for such use.

SUMMARY OF THE INVENTION

According to the present invention the unfulfilled need and the shortcomings in existing devices have been solved through the use of a system, method and apparatus, which modifies the degree of ionization by modifying the energy levels applied to the air ionization device or ionization source proportional to the change in air flow dynamics and/or air quality.

In one embodiment, an ionization air purification system for the passenger cabin of a vehicle is disclosed. The system includes an ionization device for purifying the air prior to entering into the passenger cabin of the vehicle while minimizing the production of ozone as a by-product. The system includes a control device having a potentiometer for modifying the degree of ionization by modifying the energy levels applied to the ionization device or ionization source proportional to the change in air flow dynamics or air quality. The air ionization device incorporates a glass or fiberglass dielectric member positioned between an anode and a cathode. The air ionization device is configured to produce balanced quantities of both positive ions and negative ions occurring alternately so that the ions are dispersed in an alternate fashion to avoid re-combination and opportunity to form ozone. The air ionization device is configured to operate at a voltage in the range of 1,350-4,500 VAC (volts alternating current) to minimize the ability of free electrons to convert dioxygen ($O_2$) to ozone ($O_3$).

In another embodiment, a method for purifying air circulating within the passenger cabin of a vehicle is disclosed. The method includes the following steps: (i) passing the air stream through an air ionization device for removing contaminants prior to entering into the passenger cabin of the vehicle; and (ii) modifying the degree of ionization by modifying the energy levels applied to the ionization tube or ionization source proportional to the change in air flow dynamics and air quality.

In another embodiment, a method of removing microbial contaminants from a cabin air filter without removing the filter from the vehicle is disclosed. The method includes the following steps: (i) initiating a program that allows an air ionization device to operate for a predetermined time period with the car and blower off to allow a concentration of ions to interact with the microbial contaminants in the cabin air filter; and (ii) terminating the program after the predetermined time period has ended.

Although the invention is described specifically with regard to transportation such as cars, trucks, buses, trains and planes, it would as well have applicability to other environments having to address similar variations in air flow or air quality.

The systems described can either be self contained or incorporated within existing systems.

BRIEF DESCRIPTION OF THE DRAWINGS

FIG. 6 is a schematic showing the electronic arrangement of FIGS. 5A-5B.

DETAILED DESCRIPTION OF PREFERRED EMBODIMENTS OF THE INVENTION

Without regard to the type of transportation under consideration each type typically includes an air intake system with or without a physical filter; a plenum chamber for the receipt of the air being taken in; a damper or other closure which either seals off the intake of outside air or permits the use of recirculated air; and air control fans or other devices which circulate the air through a series of ducts which eventually have outlets so as to provide the air to enter into the passenger cabin of the vehicle.

Figure 1:
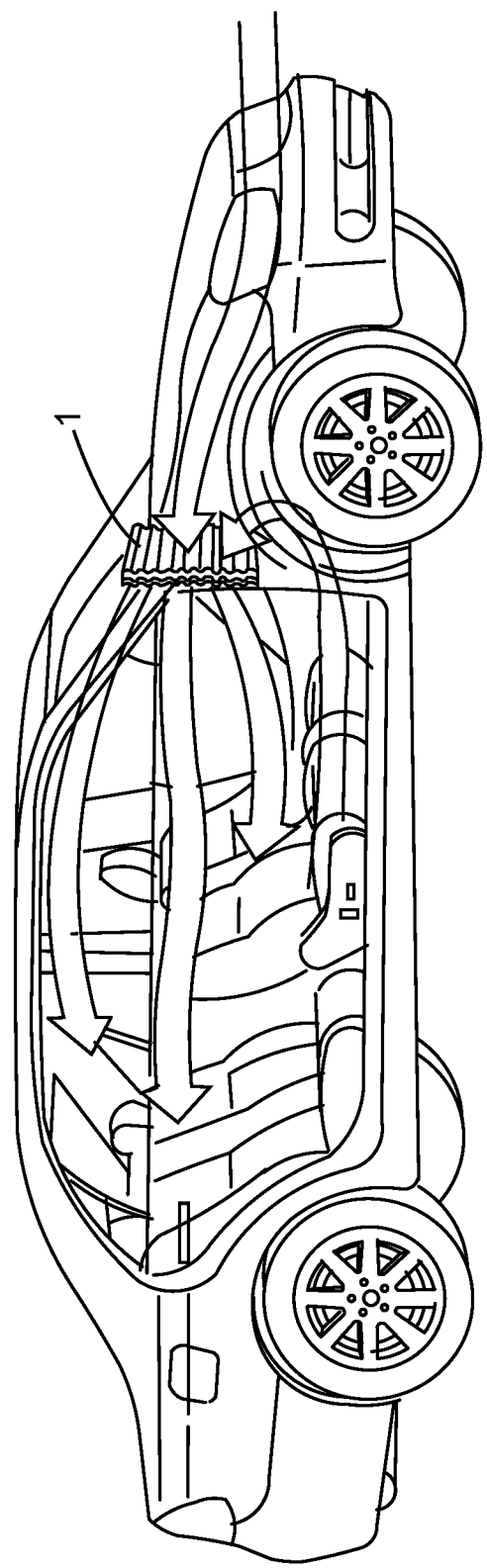
FIG. 1 depicts in general schematic form the air flow system within a typical passenger automobile.
Figure 2:
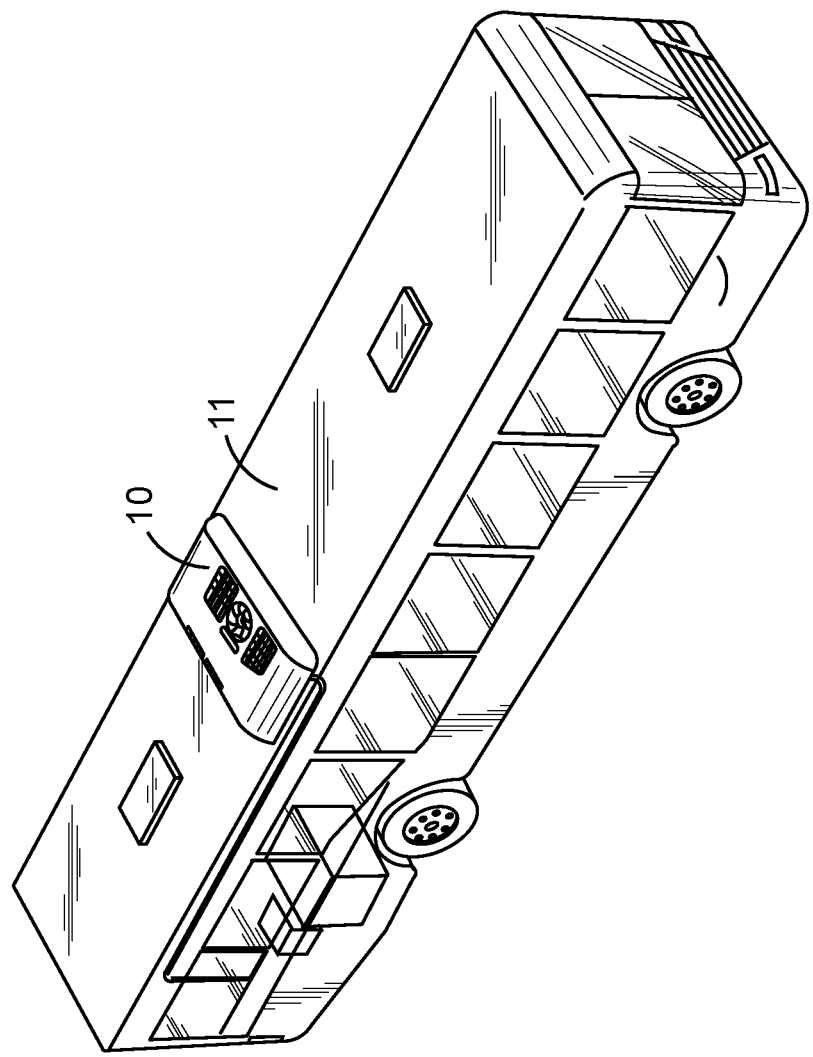
FIG. 2 depicts an air flow system as might be found typically in a passenger bus.
Figure 3:
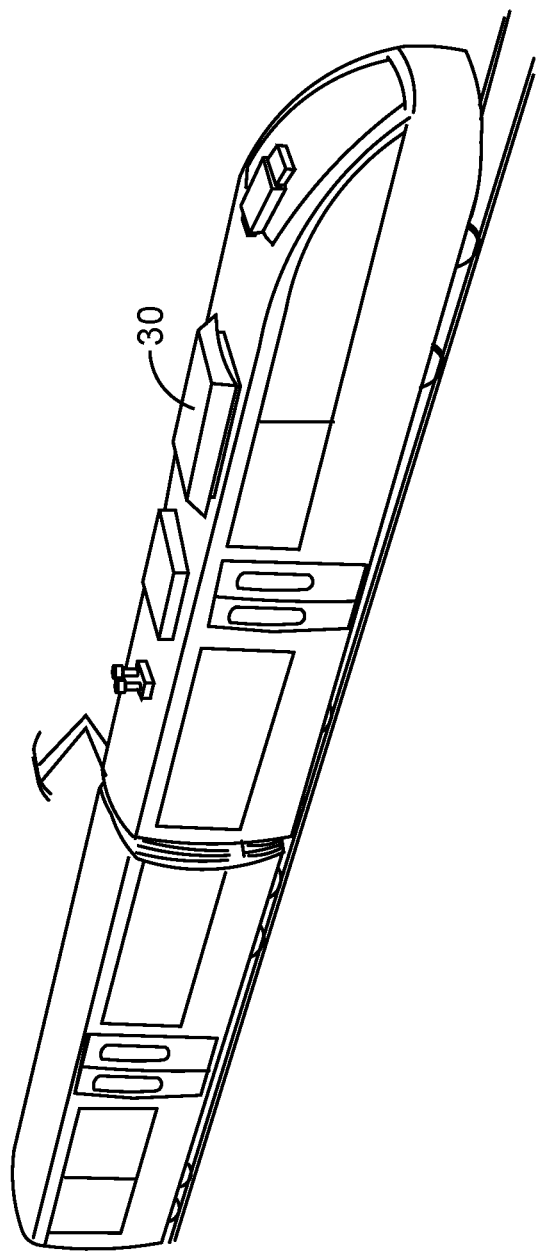
FIG. 3 depicts schematically an air flow system as may be encountered typically in a passenger train.
Figure 4:
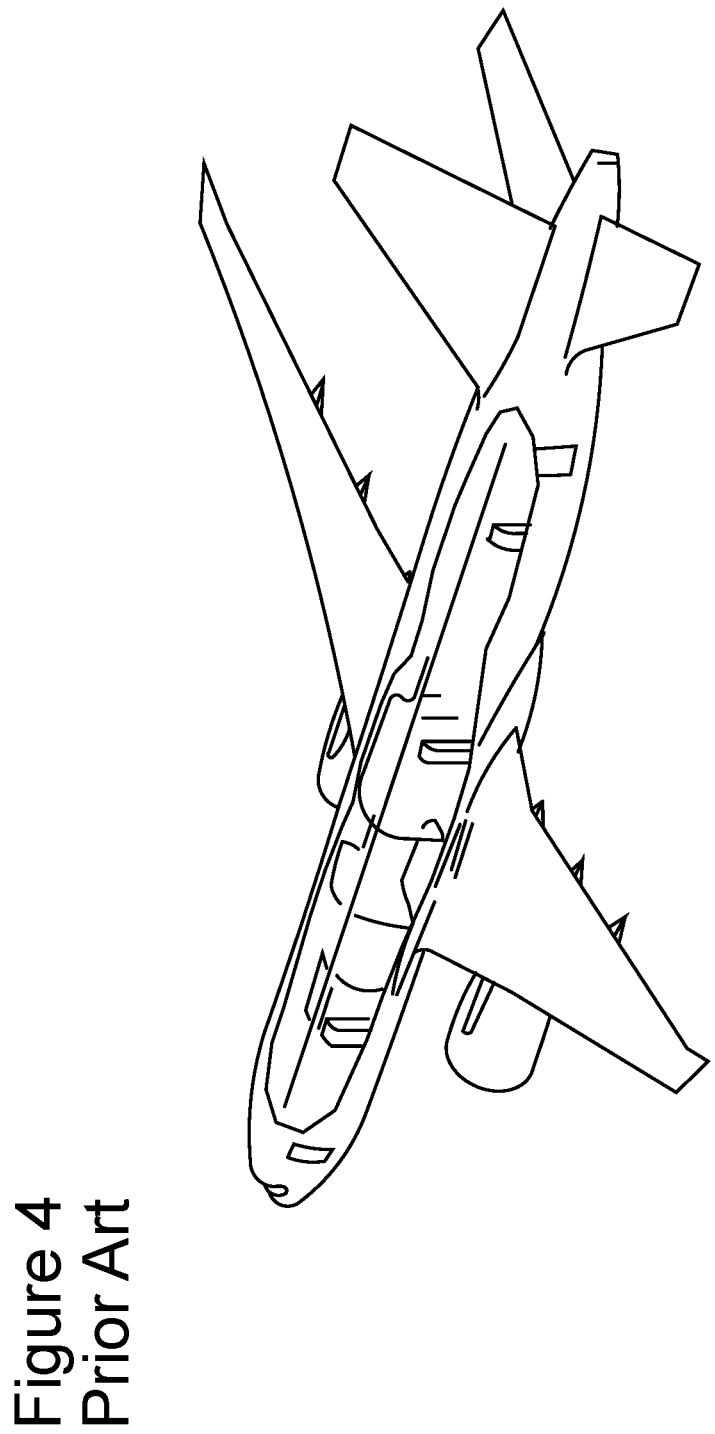
FIG. 4 depicts an air flow system as typically found in a passenger aircraft.
Figure 5A:
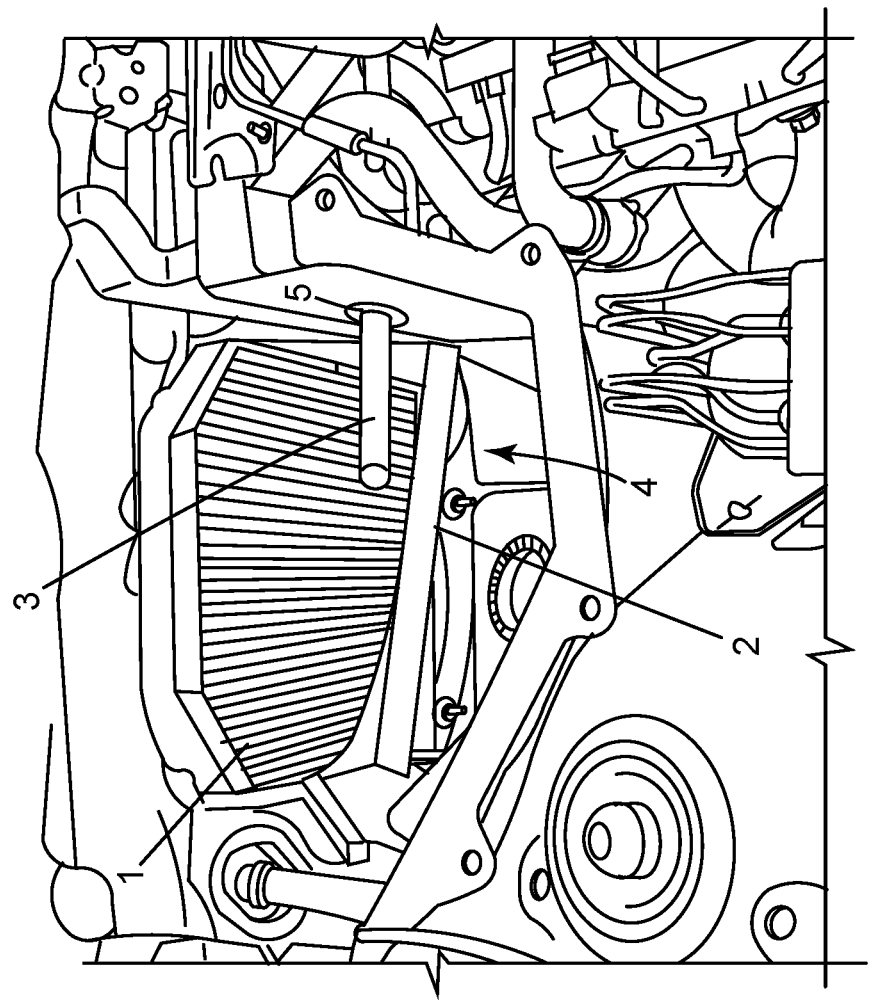
FIG. 5A is a depiction of a plenum chamber such as might be found in a passenger vehicle, such as a car or truck, in which an air ionization device having a tubular dielectric member is mounted, in accordance with a first embodiment of the invention.

FIG. 5A illustrates a first embodiment of the present invention, as implemented into the engine compartment of an automobile. As illustrated, a plenum chamber 4 is positioned within the engine compartment of the automobile, and is shown with the cover panel (not shown) removed. An air ionization device 3 having a tubular dielectric member is fixedly mounted to a sidewall of the plenum chamber 4 so as to extend into the air flow from the intake, which in the case of an automobile (as shown in FIG. 1) generally is located along the base of the windshield as that location tends to reduce the extent of the intake of pollution in the outside air. The cabin air filter 1 is shown positioned against a sidewall of the plenum chamber 4 towards the passenger cabin and a filter housing 2.

As further illustrated in FIG. 5A, the air ionization is performed using an ionization device 3 having a tubular dielectric member, but it is also contemplated that the ionization may be accomplished through other known forms of ionization generation. Importantly, the ionization device of the present invention provides a sufficient level of ionization to effectively address the contaminants, while minimizing the production of ozone, $O_3$, as a by-product. As illustrated, the ionization tube 3 is in turn secured via a socket assembly 5 that is mounted to a sidewall of the plenum chamber 4 and is electrically coupled generally via hard wiring to the 12 volt system that operates in the vehicle. A control device modifies the degree of ionization by modifying the energy levels applied to the ionization tube or ionization source proportional to the change in air flow dynamics or air quality.

Figure 5B:
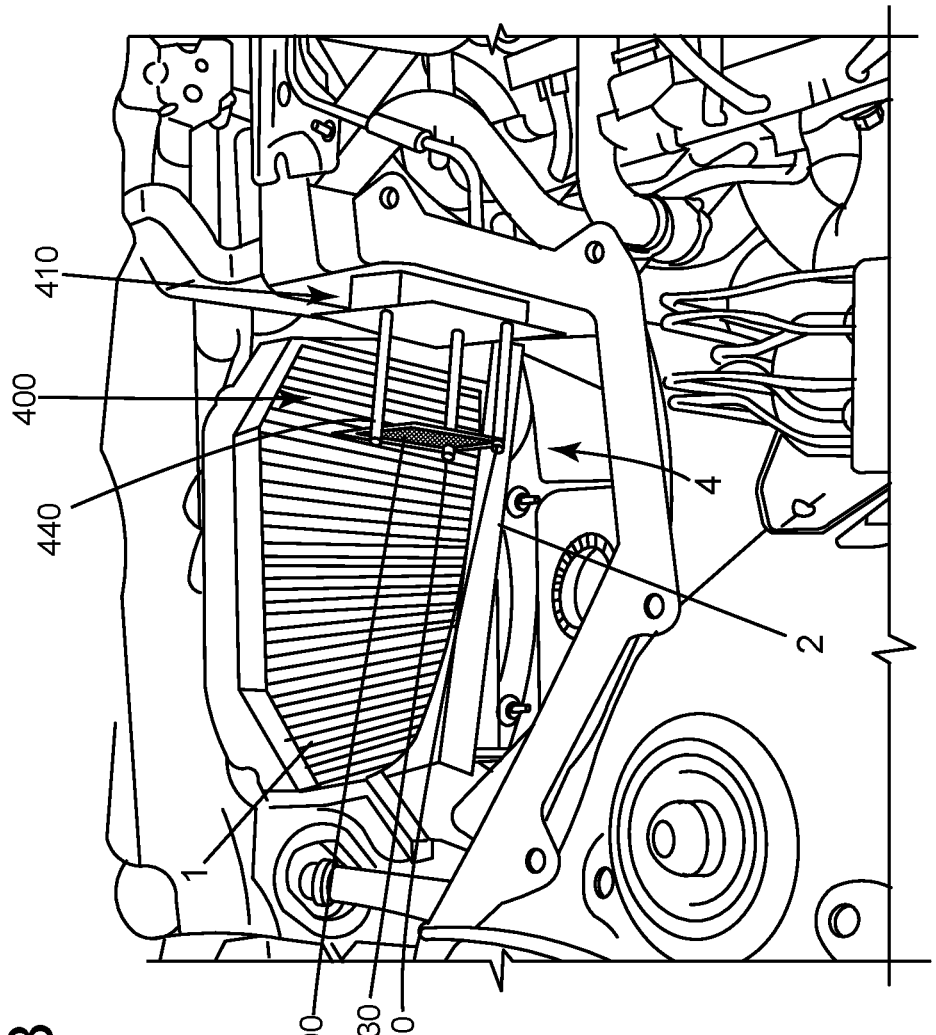
FIG. 5B is a depiction of a plenum chamber such as might be found in a passenger vehicle, such as a car or truck, in which an air ionization device having a planar dielectric member is mounted, in accordance with a second embodiment of the invention.
Figure 7A:
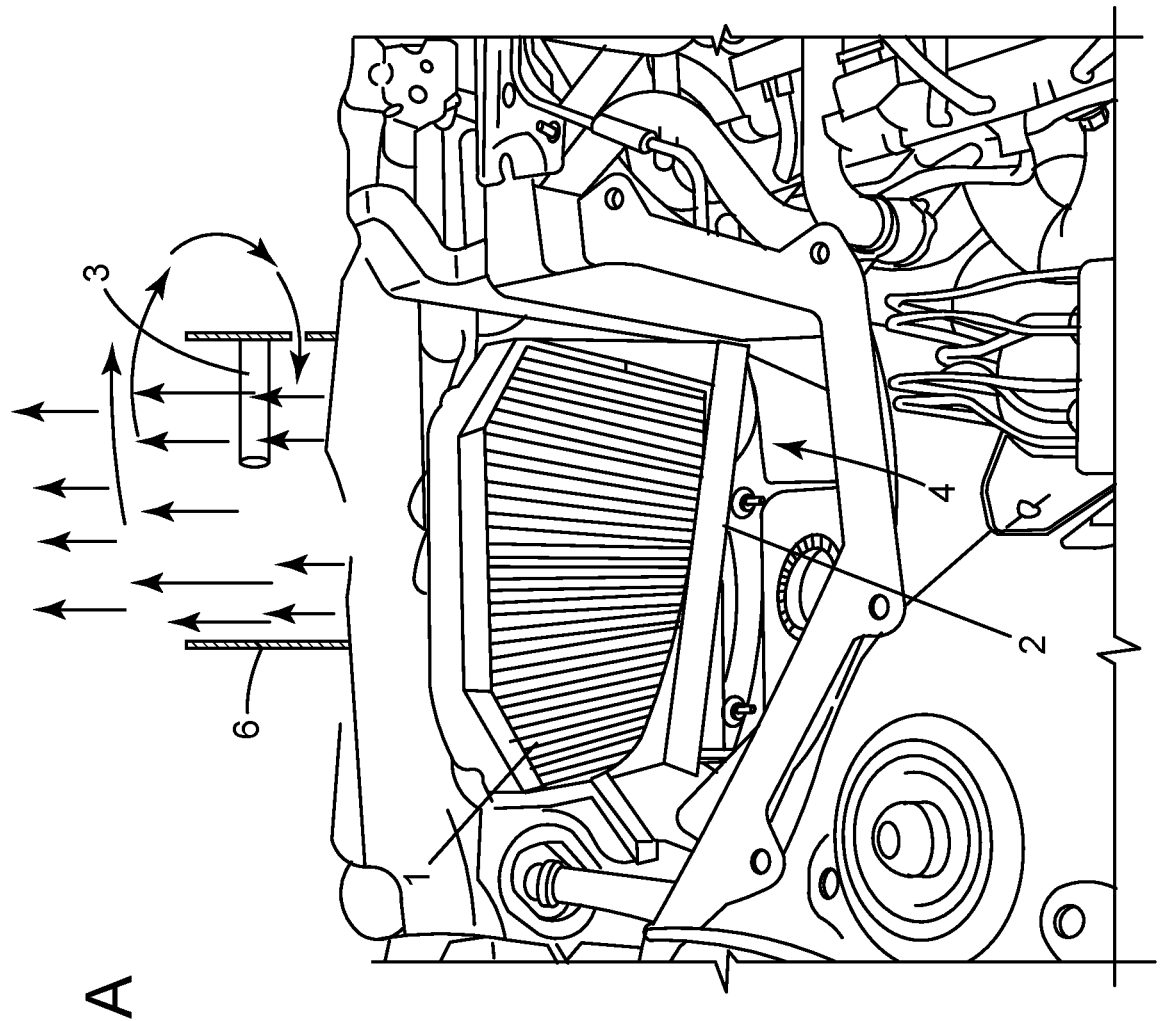
FIG. 7A is a depiction of a main air circulation duct such as might be found in a passenger vehicle, such as a car or truck, in which an air ionization device having a tubular dielectric member is mounted, in accordance with a third embodiment of the invention.
Figure 7B:
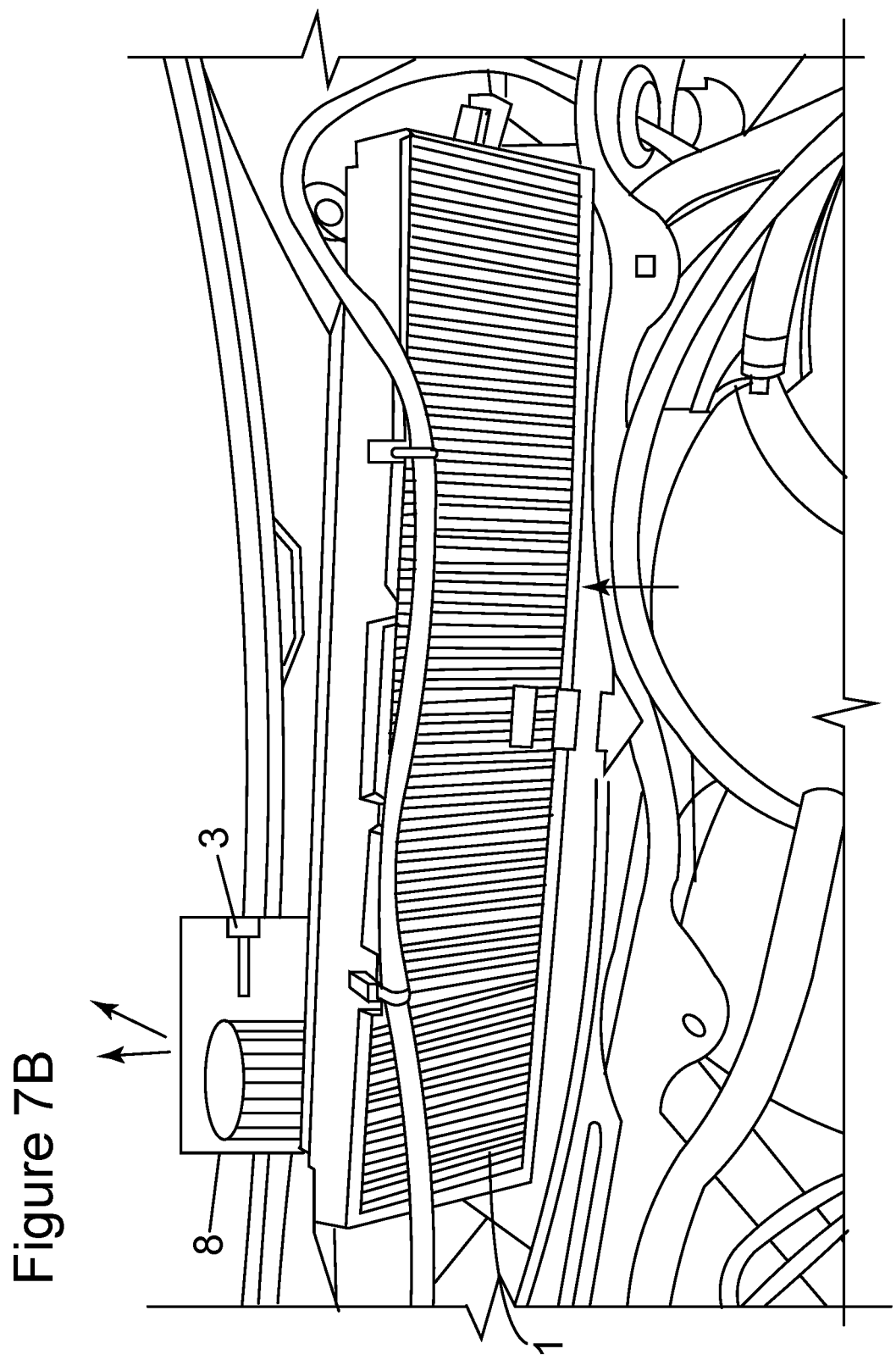
FIG. 7B is a depiction of an auxiliary mounting chamber such as might be found in a passenger vehicle, such as a car or truck, in which an air ionization device having a tubular dielectric member is mounted, in accordance with a fourth embodiment of the invention.
Figure 7C:
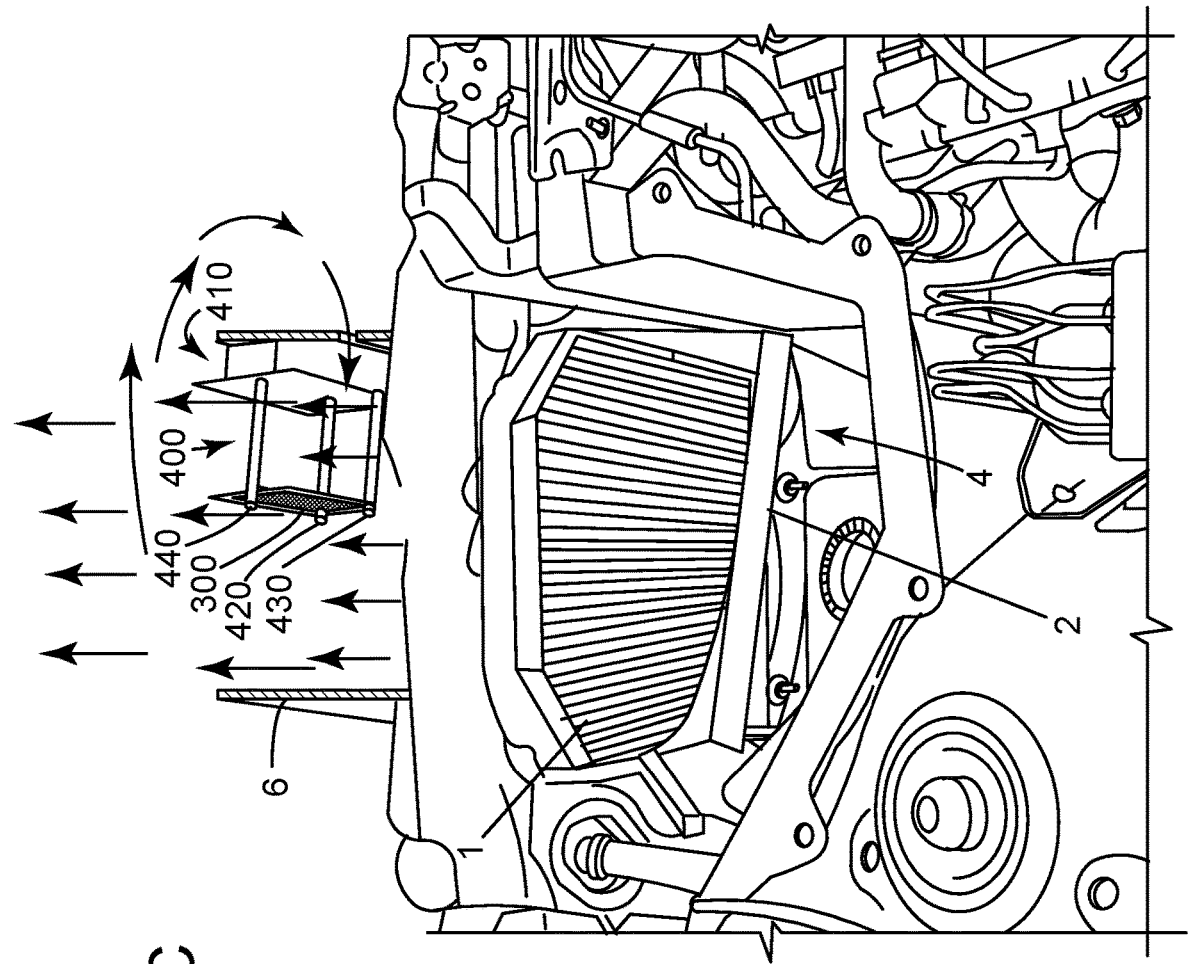
FIG. 7C is a depiction of a main air circulation duct such as might be found in a passenger vehicle, such as a car or truck, in which an air ionization device having a planar dielectric member is mounted, in accordance with a fifth embodiment of the invention.
Figure 7D:
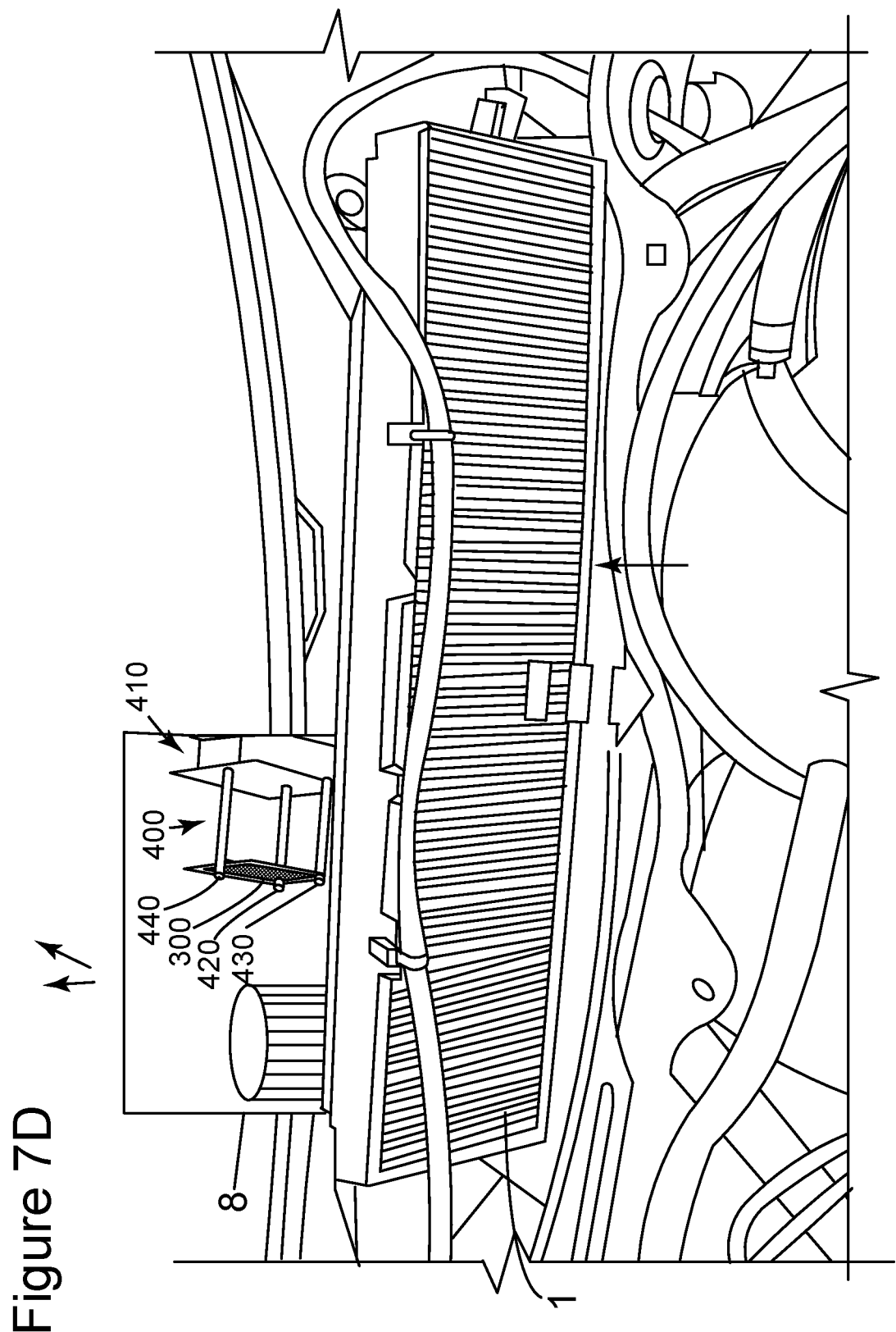
FIG. 7D is a depiction of an auxiliary mounting chamber such as might be found in a passenger vehicle, such as a car or truck, in which an air ionization device having a planar dielectric member is mounted, in accordance with a sixth embodiment of the invention.

As illustrated in FIG. 5B, a second embodiment of the invention is illustrated wherein the ionization device 400 has a planar dielectric member 300. Importantly, the ionization device of the present invention provides a sufficient level of ionization to effectively address the contaminants, while minimizing the production of ozone, $O_3$, as a by-product. As illustrated, the ionization device 400 is in turn secured via a plurality of stanchions 420, 430, 440 that are mounted to a baseplate on enclosure 410 that is in turn secured to a sidewall of the plenum chamber 4 and is electrically coupled generally via hard wiring to the 12 volt system that operates in the vehicle. A control device modifies the degree of ionization by modifying the energy levels applied to the ionization tube or ionization source proportional to the change in air flow dynamics or air quality. It is preferred that planar dielectric member 300 be mounted such that it is substantially parallel to the direction of airflow to provide a more aerodynamic position and avoid unwanted turbulence and drag on the airflow. This orientation also allows the air ionization device to more effectively scavenge the ions off the emitter.

Referring to FIG. 6, the electronics are so configured that the air ionization device 3 is controlled by the ignition switch 61, such that it is only activated upon the ignition of the vehicle and deactivated when the vehicle is turned off. As well, the ionization system is connected to the manual or automatic electronics 62 that control the volumes of air that are emitted into the vehicle—generally ranging from a low to a high speed. In addition, there is a sensor 63 which acts in the nature of a rheostat (or like device) which senses the fan speed being commanded and changes the amount of power being delivered to the tube so as to adjust the level of ionization to be commensurate with the air flow.

Referring again to FIGS. 5A and 5B, as is conventional, there is usually a damper (not shown) that closes off the air flow from the plenum chamber 4 from the interior of the vehicle. As a result, outside air is not supplied to the passenger cabin. Instead, the air within the vehicle is being recirculated. Although the recirculated air has been treated, the closing of the damper will as well seal off the ionization tube from the air flow. Preferably the closure of the damper will as well cause a switch (not shown) to shut down the power to the ionization tube.

Referring to FIGS. 7A-7D, alternative embodiments are shown. Where it is desired that the ionization continue to operate for the recirculated air, the air ionization device, rather than be mounted in the plenum chamber 4, is mounted within a main air circulation duct 6 (see air ionization device 3 in FIG. 7A and air ionization device 400 in FIG. 7C) which is downstream from the damper (not shown) and within the recirculating air flow stream. In other embodiments, the air ionization device is mounted within an auxiliary mounting chamber 8 (see air ionization device 3 in FIG. 7B and air ionization device 400 in FIG. 7D).

Figure 8:
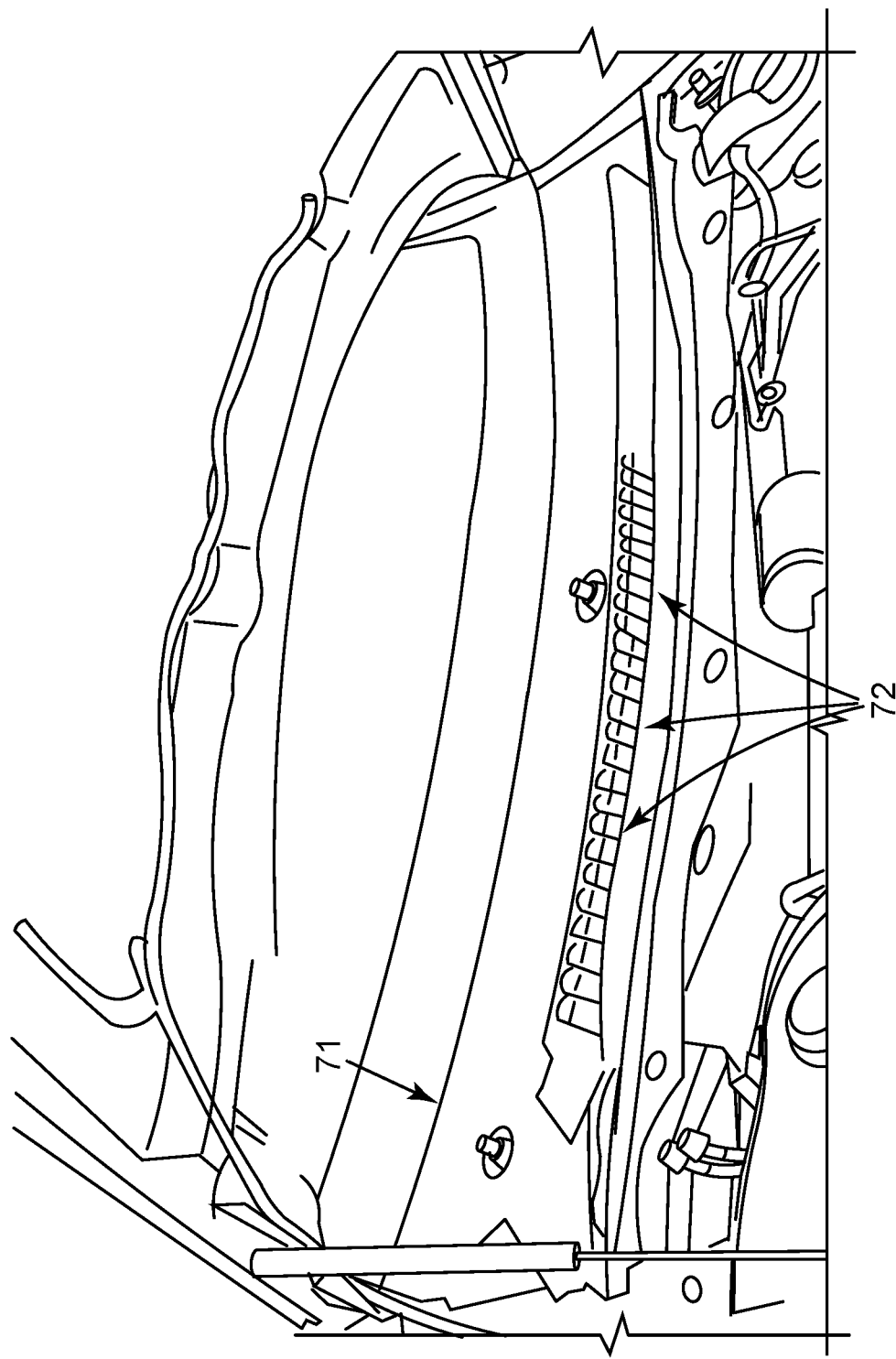
FIG. 8 illustrates a cowl grill such as might be found positioned near the passenger cabin of a passenger vehicle, such as a car or truck and includes an outside air intake that acts as an inlet for the air conditioning system of the vehicle.

As shown in FIG. 8, a cowl grill 71 is positioned near the passenger cabin of the vehicle and includes an outside air intake 72 that acts as an inlet for the air conditioning system of the vehicle.

Preferably the control system for the power to the ionization tube in the recirculation mode is reduced so as to lessen the degree of ionization to be proportional to the desired degree of ionization, given that the air being circulated has been preconditioned but nonetheless may be subject to gaseous contaminants present in the interior of the vehicle such as, for example, as might be encountered by smoking.

In newer passenger cars, cabin air filters have become increasingly standard. These are typically pleated media filters 1 as shown in FIGS. 5A and 5B. These filters are intended to trap airborne contaminants from the air entering the car. Mold and bacteria grow on these over time especially since outside air can be laden with moisture which can foster microbial growth. In another embodiment, the present invention can offer a "clean mode" feature that would allow the unit to operate for a set period of time with the car and blower off to allow a concentration of ions to interact with the microbial contaminants in the cabin air filter. This can be a user enabled function. An automated message on the car information screen can remind the car owner to run this "clean mode" feature.

The following discussion relates in particular to the embodiments of the present invention that utilize an air ionization device having a planar dielectric member and the ability of such a device to purify the air while minimizing the production of ozone as a by-product.

Description of Air Ionization Device Having a Planar Dielectric Member:

Consisting of a flat plate Bi-polar ionization emitter of varying square inches of emitter surface, based on the air flow capacity. This flat plate emitter can be of varying shapes and configurations from square to rectangular, round, and or polygonal in shape. Typically about 2 to 100 square inches of emitter surface area. This Bi-Polar Ion emitter includes a impervious, non-porous, dielectric fiberglass FR-4 or G-10 material that has a series of conductive deposited substrates bonded permanently to the anterior surface of one side of the Flat Plate Emitter (FPE), a grid of a multitude of 6-pointed stars of 4 mm across the widest corners of the stars. The stars are symmetrically spaced at 2 mm intervals in X and Y directions. The conductive substrate deposition is typically layers of copper then nickel and gold. This is called the ANODE of the FPE. The thickness of the dielectric barrier can vary by intended ion output, input/output voltage and significant reduction of ozone emissions.

The Cathode of the FPE includes a continuous deposition metal conductive substrate bonded to the posterior side of the plate. The Cathode is slightly smaller than the square inches of the ANODE. This difference in size is a further contributor to low ozone formation and emissions. The conductive deposition is typically layers of copper-nickel and gold.

Each of the Anode and Cathode have a power transmission tape or terminal strip bonded directly to the fiberglass dielectric. The FPE is driven by a solid state fly-back electronic control printed circuit board, utilizing 9-12 VDC input. Directly from this printed circuit board is a converter that can supply 9-12 VAC (volts alternating current) input power to the transformer that boosts the output voltage to the FPE to between 1350-4500 VAC (volts alternating current). This step-up in voltage is directly proportional to the input voltage to the transformer. The printed circuit board is self-regulating and pulses current to the transformer via Mosfet controllers and a capacitive discharge system. The system settles to a steady state voltage between 1350 and 4500 VAC (volts alternating current).

Operation:

Once the FPE receives the proper voltage, Bi-Polar Ions are emitted continuously from the points of each 6-pointed star. Airflow created by the air-handling unit/fan in a typical passenger cabin of a vehicle is set to impinge at an angle onto the ANODE, Ions are liberated and then carried into the air-stream providing continuous air cleaning odor reduction and sanitization of the cabin of a vehicle. This is then carried through the normal and existing ducting into the cabin.

Benefits:

Bi-polar Ionization provides continuous sanitization, total volatile organic compounds (T.V.O.C.) breakdown, odor reduction and particulate agglomeration greatly befitting passengers in the vehicle. This system has very low ozone emissions and very high Bi-polar ion emissions. The system utilizes virtually all variations of input power from a vehicle from 9 VDC to, but not only, 48 VDC. The difference in input voltage is variable by design and intended application.

Location of Installation:

A typical passenger vehicle air-handling system includes an air-intake system usually placed in a high pressure area of the vehicle dynamically and an air channel leading to, but not always, a filter, thence to a plenum chamber consisting of air-management doors and diverters, allowing the air supply to be delivered to windshield for defrosting, passenger comfort through ducts. In the plenum chamber a fan is present to provide airflow when the vehicle is moving slowly or not-at-all. Within the air-handling system is usually water to water heater cores and cooling air-conditioning evaporator cores.

The following discussion relates in particular to the embodiments of the present invention that utilize an air ionization device having a tubular dielectric member and the ability of such a device to purify the air while minimizing the production of ozone as a by-product.

According to U.S. Patent Application Publication No. US 2010/0247389 A1 entitled "Bipoloar Ionization Tube" at paragraph [0011], it is known that ozone ($O_3$) can be a by-product of the air ionization process, sometimes deliberate, sometimes consequential. Since the present application is to provide ionized air into the passenger cabin, minimizing or eliminating ozone generation is desired. The air ionization device utilizes balanced quantities of both positive and negative charges occurring alternately so that the ions are dispersed in an alternate fashion to avoid re-combination and opportunity to form ozone. Also, the air ionization device having a tubular dielectric member uses low voltage, in the range of 2,000-2,500 VAC, (voltage alternating current), in the present application which will lessen the chance of free electrons to convert $O_2$ to $O_3$. This is possible by the design of the air ionization device. The combination of electronic design, device design and tube design all allow for ion saturation in an enclosed space without the formation of any unsafe levels of ozone. This has been tested by Intertek in testing the present technology to standard UL 867 Revision 2013 which is the laboratory test method for ozone emissions.

As discussed below, the various embodiments of the present invention can be implemented into other types of passenger vehicles including, without limitation, buses, trains, and airplanes.

Figure 9:
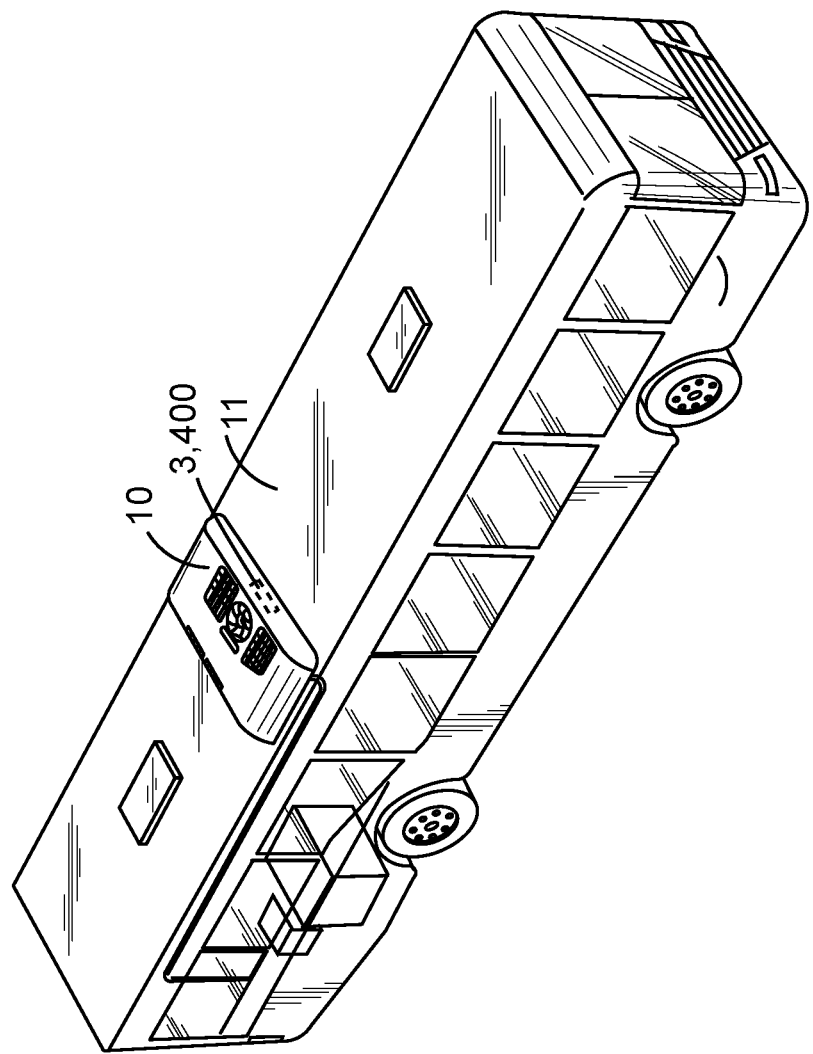
FIG. 9 is a depiction of a typical passenger bus ventilation system, in which an air ionization device is mounted, in accordance with the present invention.
Figure 12:
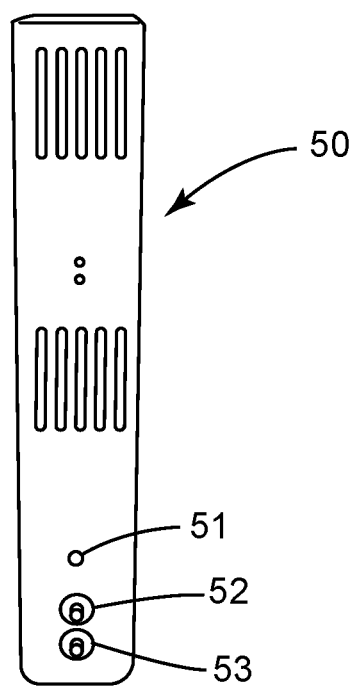
FIG. 12 illustrates an example of a suitable ionization self contained unit that can be used in certain embodiments of the invention.

Referring to FIG. 9, the air ionization device 3 or 400 of the present invention can be positioned within the air circulation system 10, located on the roof 11 of a passenger bus. Although the air flow and desired ionization environment employed is substantially the same as that described with regard to passenger cars, given the size of the interior of a passenger bus, train, or airplane and the likelihood that it would be in operation for a continuous extended period of time with a greater likelihood of encountering physical and gaseous contaminants, a preferable system for buses, trains, or airplanes includes the mounting of a series of ionization self contained units along, for example, the upper side walls above the windows or along the interior ceiling of the bus, train or airplane. One such example of a suitable ionization self contained unit 50 is illustrated in FIG. 12, which includes a power indicator 51, an ion level control 52, and a fan speed control 53. The controls can be automated into the system in one embodiment. In another embodiment, the controls can be operated by the driver through a centralized control unit. An exemplary commercially available ionization unit is sold by the assignee of the present invention as model number ATMOSAIR T400WM, currently available at www.atmosair.com.

Although the individual units are self contained, they are coupled with the 12 volt system of the bus (although an auxiliary power supply could also be used). In the preferred embodiment, the same general type of sensing devices in terms of air flow and air quality described with respect to cars is employed to modify the amount of ionization for each of the units, either individually or collectively.

Figure 10:
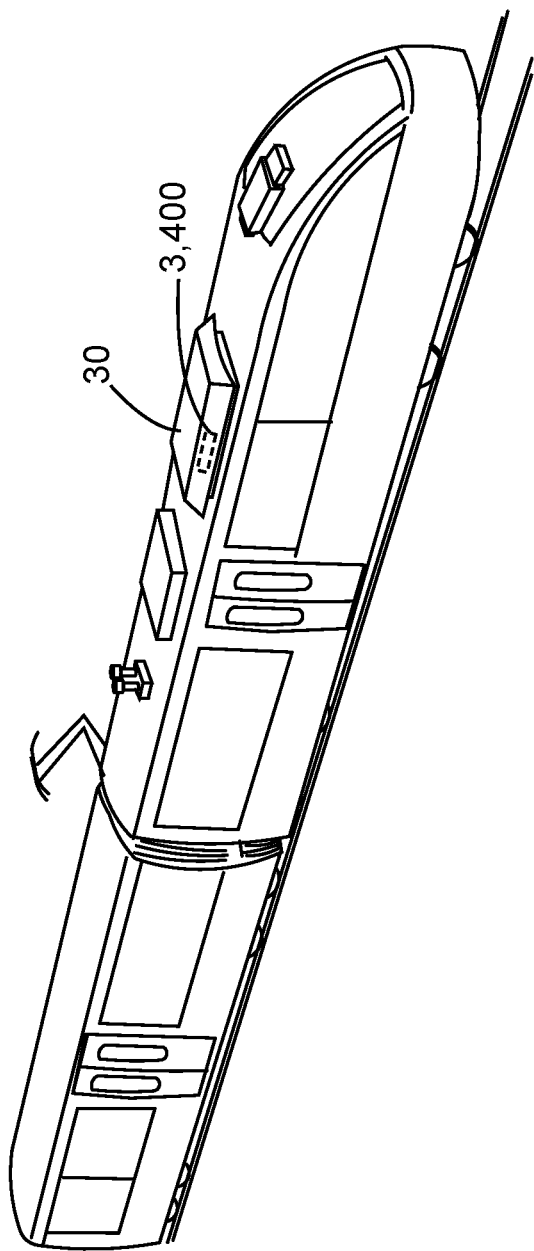
FIG. 10 is a depiction of a typical passenger train ventilation system, in which an air ionization device is mounted, in accordance with the present invention.

As illustrated in FIG. 10, a system, not dissimilar from that described with regard to the buses is illustrated for passenger trains. Various sensors determine air flow and air quality and whether the system is in a fresh air or air circulation mode. The air ionization device 3 or 400 of the present invention can be positioned within the air circulation systems 30.

Figure 11:
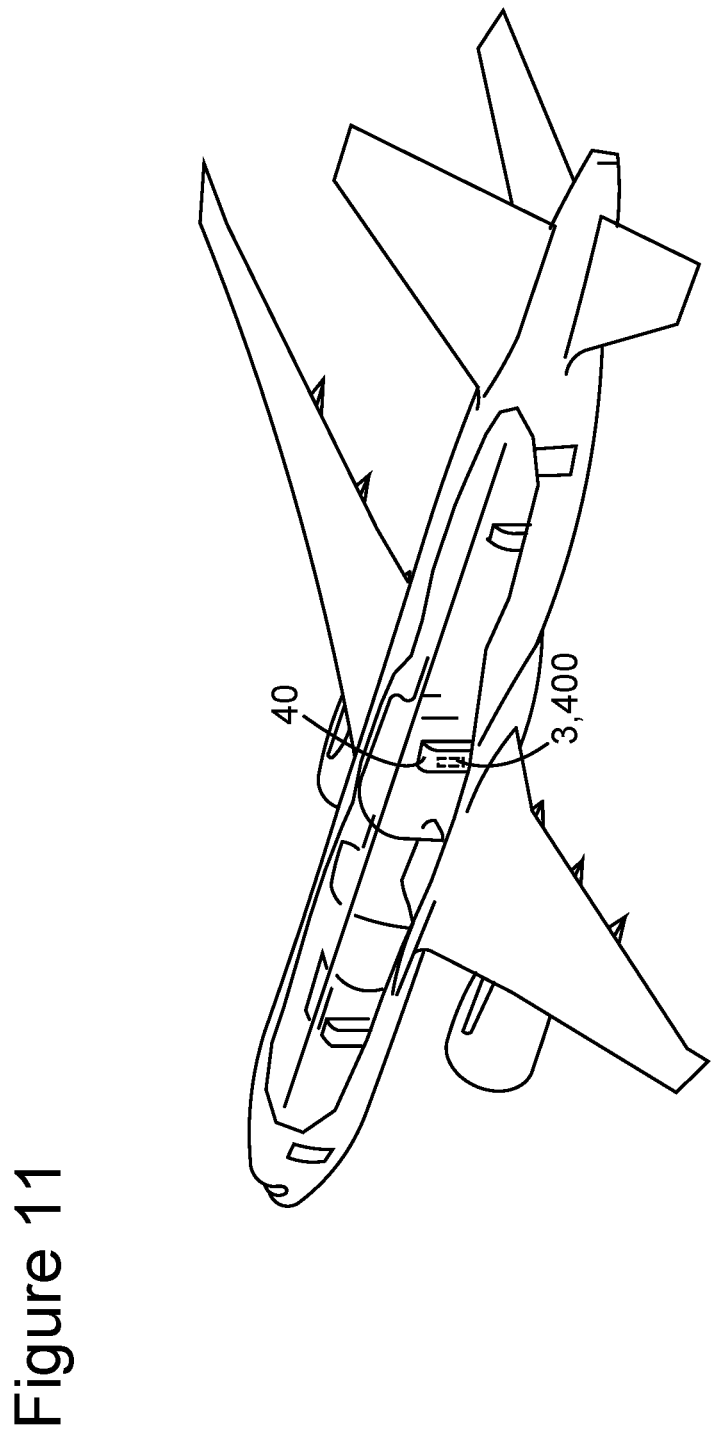
FIG. 11 is a depiction of a typical passenger plane ventilation system, in which an air ionization device is mounted, in accordance with the present invention.

Referring next to FIG. 11, the air circulation system in most passenger planes generally has air flow controls which can be turned on or off—or modified as to the degree of flow—by individual passengers at their seats. Once the plane is airborne the system is generally a recirculation system. Indeed there is much discussion in literature that the constant recirculation of unpurified air within air craft has had adverse affects upon the health of passengers as they are constantly exposed to the same recirculated air. The air ionization device 3 or 400 of the present invention can be positioned within one or more bulkhead ventilation units 40 for purifying the air.

Thus, the systems previously described can be used within the plane, but the preferable system has the ionization tube or multiple tubes or other ionization source mounted within the ducts that feed the exit orifices, are downstream from the initial air intake and downstream from the damper or cutoff valving that closes off the air circulation from the outside sourcing of air, but upstream from the air shut off valves at the passengers' seats.

It should be understood that the present invention can be used in a passenger vehicle both while it is stationary and while it is moving.

The above disclosure is intended to be illustrative and not exhaustive. This description will suggest many modifications, variations, and alternatives may be made by ordinary skill in this art without departing from the scope of the invention. Those familiar with the art may recognize other equivalents to the specific embodiments described herein. Accordingly, the scope of the invention is not limited to the foregoing specification.

What is claimed is:

1. An ionization air purification system for a passenger cabin of a vehicle comprising:
    an air ionization device for purifying an air stream while minimizing production of ozone as a by-product; and
    a control device configured to adjust a degree of ionization by modifying energy levels applied to the ionization device;
    wherein the air ionization device incorporates a glass or fiberglass dielectric member positioned between an anode and a cathode;
    wherein the air ionization device is configured to produce balanced quantities of both positive ions and negative ions occurring alternately so that the ions are dispersed in an alternate fashion to avoid re-combination and opportunity to form ozone;
    wherein the air ionization device is configured to operate at a voltage in a range of 1,350-4,500 VAC (volts alternating current) to minimize a conversion by free electrons of dioxygen to ozone,
    wherein in a first mode of operation, the control device is configured to control the passage of the air stream through the air ionization device to remove contaminants prior to entering into the passenger cabin of the vehicle, and to adjust the degree of ionization by modifying the energy levels applied to the ionization device proportional to a change in air flow dynamics and air quality; and
    wherein in a second mode of operation, the control device is configured to operate the air ionization device for a predetermined period of time with the vehicle turned off and with an air blower for the air stream turned off, in order to allow a concentration of ions from the air ionization device to interact with microbial contaminants in a cabin air filter.

2. The ionization air purification system of claim 1, wherein the vehicle is a passenger automobile.

3. The ionization air purification system of claim 2, wherein the air ionization device is mounted within a plenum chamber located within an engine compartment of the passenger automobile.

4. The ionization air purification system of claim 2, wherein the air ionization device is mounted within an auxiliary mounting chamber that is adapted for use with a recirculating air flow stream within the passenger cabin.

5. The ionization air purification system of claim 1, wherein the vehicle is a passenger bus.

6. The ionization air purification system of claim 1, wherein the vehicle is a passenger train.

7. The ionization air purification system of claim 1, wherein the vehicle is a passenger plane.

8. The ionization air purification system of claim 1, wherein the dielectric member is a tube.

9. The ionization air purification system of claim 8, wherein the air ionization device is electrically coupled to an on-board electrical system that operates in the vehicle.

10. The ionization air purification system of claim 9, further comprising a switch for selectively activating the air ionization device.

11. The ionization air purification system of claim 1, wherein the dielectric member is a flat board.

12. The ionization air purification system of claim 11, wherein the air ionization device is electrically coupled to an on-board electrical system that operates in the vehicle.

13. The ionization air purification system of claim 12, further comprising a switch for selectively activating the air ionization device.

14. The ionization air purification system of claim 1, wherein the control device includes a sensor which senses the air flow dynamics and modifies the energy levels being delivered to the ionization device.

15. The ionization air purification system of claim 1, wherein the control device includes a sensor which senses the air quality and modifies the energy levels being delivered to the ionization device.

16. The ionization air purification system of claim 11, wherein the flat board comprises an impervious, non-porous, dielectric fiberglass material that has a series of conductive deposited substrates bonded permanently to one side of the flat board.

17. The ionization air purification system of claim 16, wherein the conductive deposited substrates comprise a grid of a multitude of 6-pointed stars, symmetrically spaced in X and Y directions.

18. The ionization air purification system of claim 17, wherein the conductive deposited substrates are layers of copper, nickel, and gold.

* * * * *